(12) United States Patent
Boulnois et al.

(10) Patent No.: US 8,142,451 B2
(45) Date of Patent: Mar. 27, 2012

(54) ACTUATOR AND DETACHABLE CONNECTOR OF FLEXIBLE CLIP APPLIER

(75) Inventors: Jean-Luc Boulnois, Boston, MA (US); Masayasu Sato, Saitama-ken (JP); Tomohiro Kawano, Tokyo (JP)

(73) Assignee: Microline Surgical, Inc., Beverly, MA (US)

( * ) Notice: Subject to any disclaimer, the term of this patent is extended or adjusted under 35 U.S.C. 154(b) by 407 days.

(21) Appl. No.: 12/359,821

(22) Filed: Jan. 26, 2009

(65) Prior Publication Data

US 2010/0191257 A1    Jul. 29, 2010

(51) Int. Cl.
*A61B 17/10* (2006.01)
(52) U.S. Cl. ....................................................... 606/143
(58) Field of Classification Search .......... 606/139–143; 227/175.1–182.1; 623/23.72
See application file for complete search history.

(56) References Cited

U.S. PATENT DOCUMENTS

| | | | |
|---|---|---|---|
| 4,658,822 A | 4/1987 | Kees, Jr. | |
| 4,966,603 A | 10/1990 | Focelle et al. | |
| 5,593,414 A | 1/1997 | Shipp et al. | |
| 5,858,018 A | 1/1999 | Shipp et al. | |
| 5,904,693 A * | 5/1999 | Dicesare et al. | 606/143 |
| 5,993,465 A | 11/1999 | Shipp et al. | |
| 6,139,555 A | 10/2000 | Hart et al. | |
| 6,290,575 B1 | 9/2001 | Shipp | |
| 6,350,269 B1 | 2/2002 | Shipp et al. | |
| 6,607,540 B1 | 8/2003 | Shipp | |
| 6,652,539 B2 | 11/2003 | Shipp et al. | |
| 6,652,545 B2 | 11/2003 | Shipp et al. | |
| 6,911,033 B2 | 6/2005 | de Guillebon et al. | |
| 7,141,056 B2 | 11/2006 | Manetakis | |
| 2002/0082615 A1 | 6/2002 | Shipp et al. | |
| 2002/0082618 A1 | 6/2002 | Shipp et al. | |
| 2004/0097972 A1 | 5/2004 | Shipp et al. | |
| 2004/0106936 A1 | 6/2004 | Shipp et al. | |
| 2005/0119677 A1 | 6/2005 | Shipp | |
| 2005/0149063 A1 | 7/2005 | Young et al. | |
| 2006/0094932 A1 | 5/2006 | Goldfarb et al. | |
| 2006/0094933 A1 | 5/2006 | Goldfarb et al. | |
| 2007/0049950 A1 | 3/2007 | Theroux et al. | |
| 2007/0185504 A1 | 8/2007 | Manetakis et al. | |
| 2007/0282355 A1 | 12/2007 | Brown et al. | |
| 2008/0114377 A1 | 5/2008 | Shibata et al. | |
| 2008/0306492 A1 | 12/2008 | Shibata et al. | |

FOREIGN PATENT DOCUMENTS

| | | |
|---|---|---|
| EP | 1757236 | 2/2007 |
| WO | 2005/011745 | 2/2005 |
| WO | 2007/142977 | 12/2007 |
| WO | 2008/045350 | 4/2008 |
| WO | 2008/045374 | 4/2008 |

OTHER PUBLICATIONS

U.S. Appl. No. 12/256,698 to Boulnois et al., filed Oct. 23, 2008.
Search report from E.P.O., mail date is Sep. 2010.

* cited by examiner

*Primary Examiner* — Melanie Tyson
(74) *Attorney, Agent, or Firm* — Greenblum & Bernstein P.L.C.

(57) ABSTRACT

A clip applier for deploying a surgical clip includes an actuator having a flexible wire and a collet chuck coupled to a piston. Further, actuation of the piston in a forward direction towards a distal end of the clip applier advances the flexible wire in the forward direction.

10 Claims, 19 Drawing Sheets

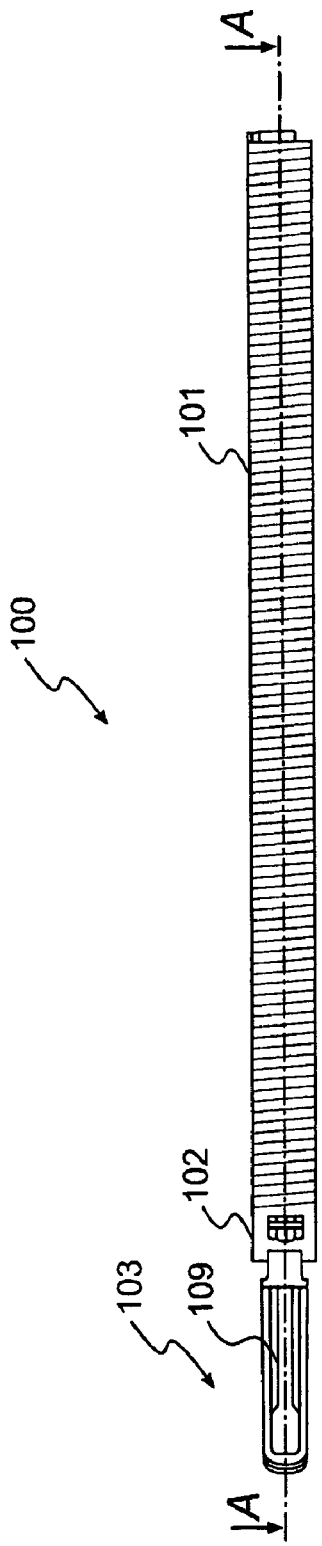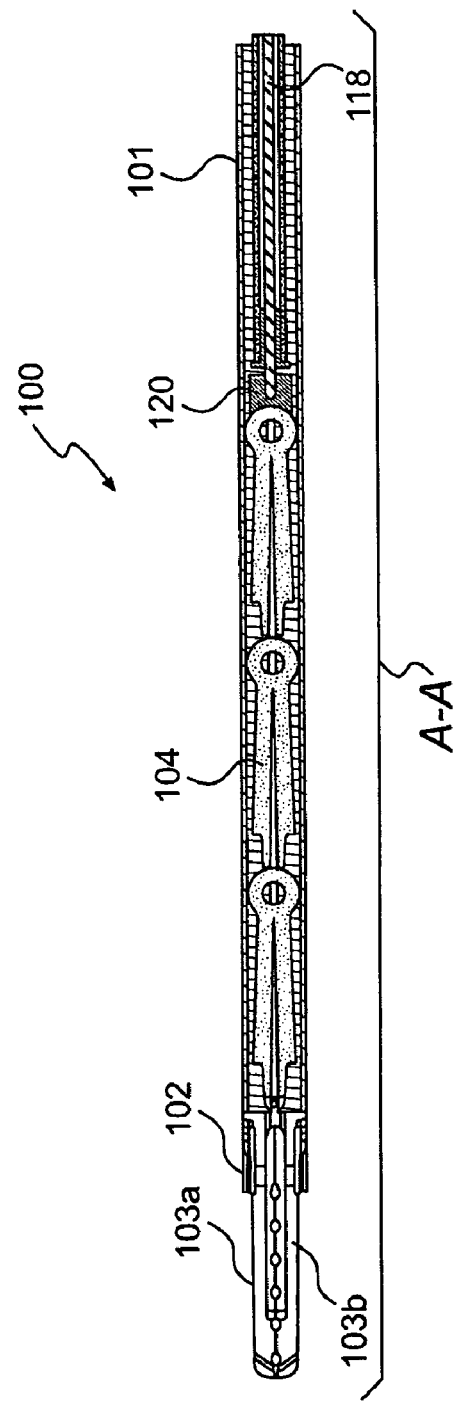

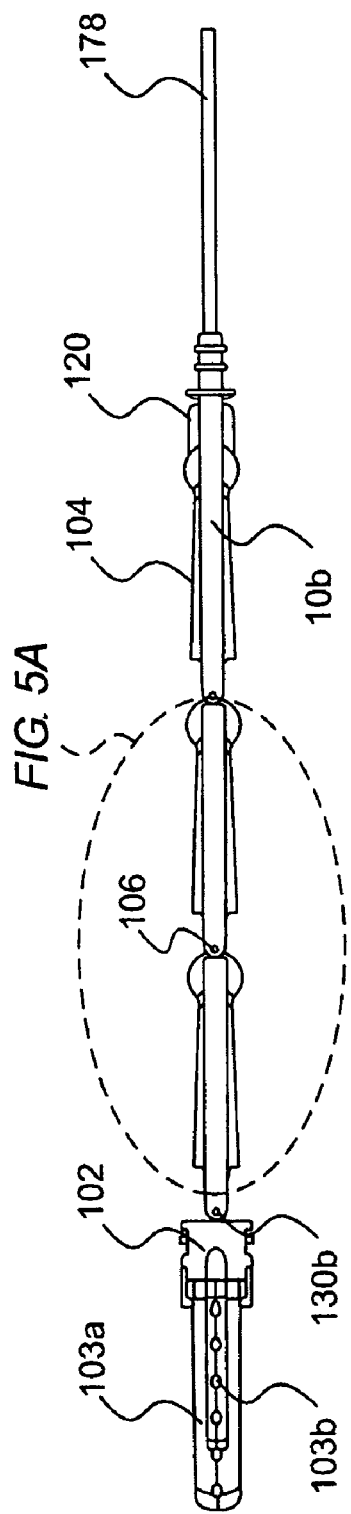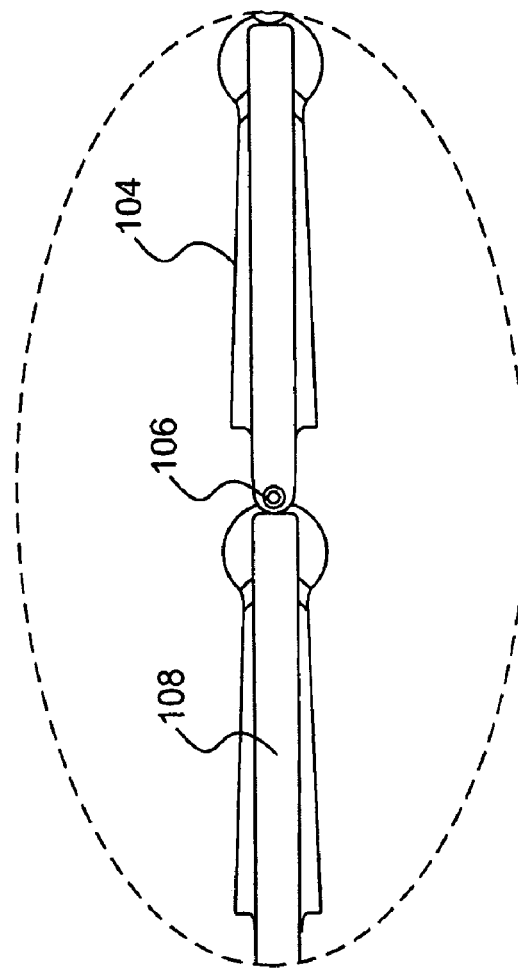
FIG. 5A
FIG. 5B

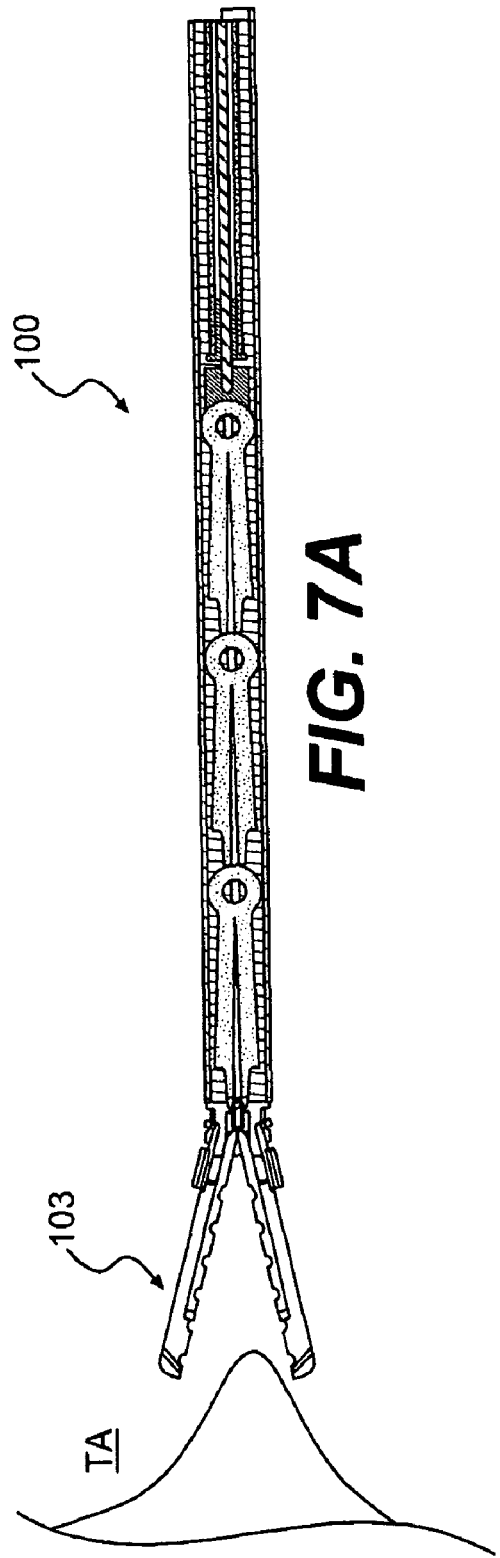
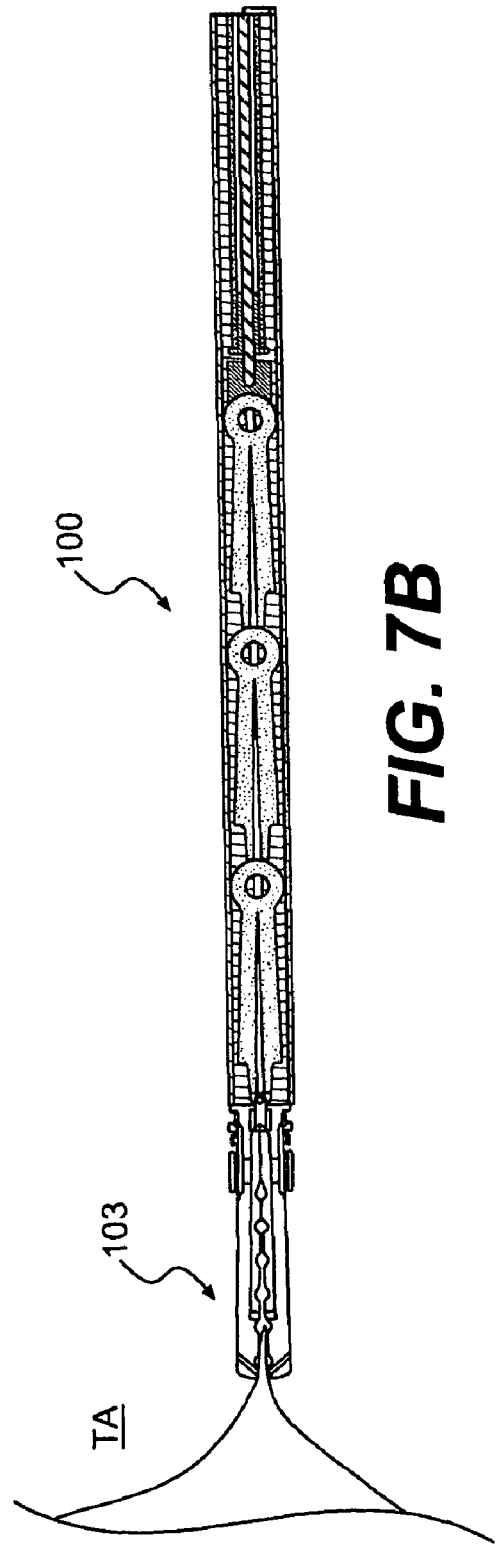

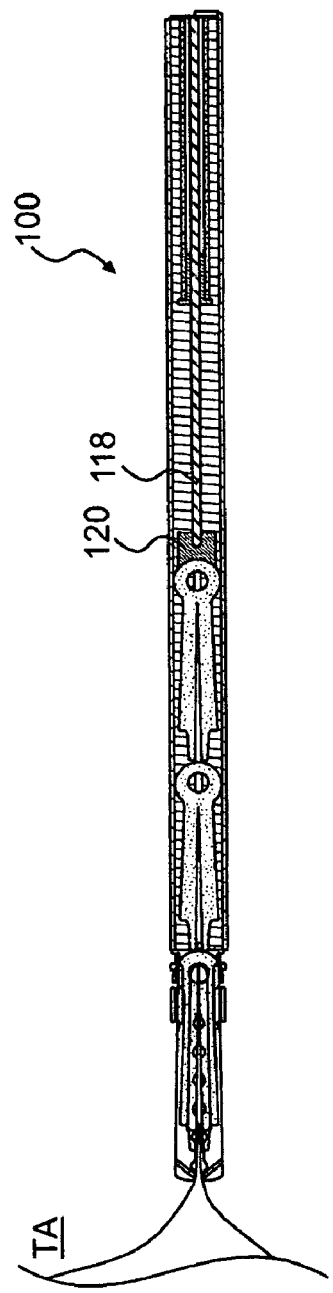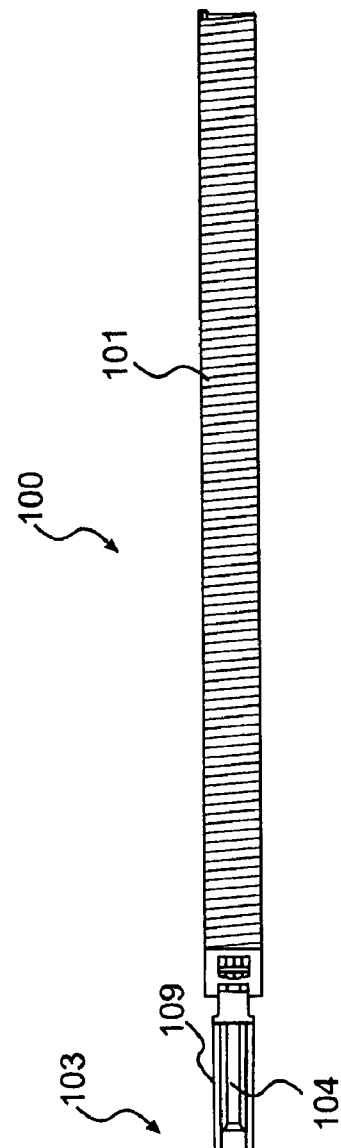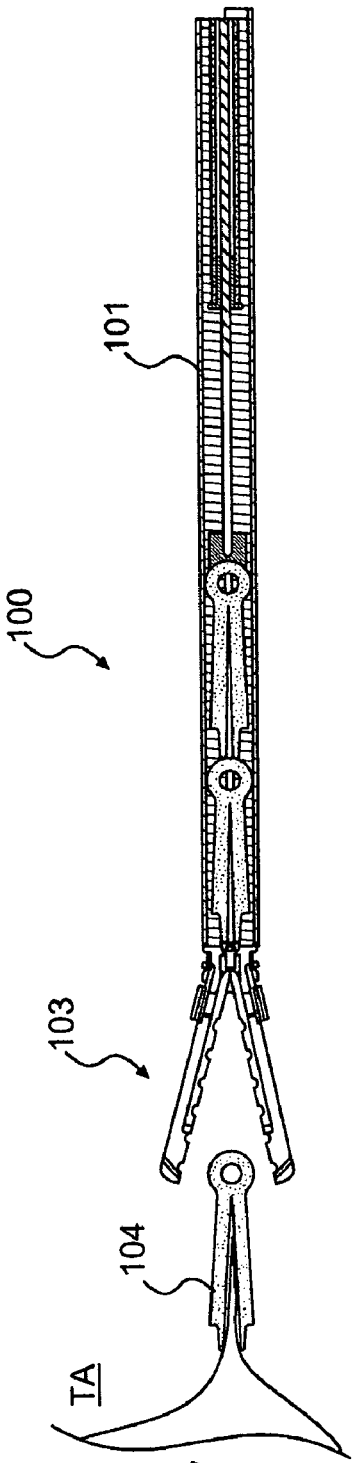

ACTUATOR AND DETACHABLE CONNECTOR OF FLEXIBLE CLIP APPLIER

BACKGROUND OF THE INVENTION

I. Field of the Invention

The present invention relates generally to an actuator and detachable connector of a flexible clip applier (e.g., for applying a surgical clip).

II. Discussion of the Background Art

Surgical instruments have been developed for use with a variety of endoscopic surgical techniques and procedures. In particular, in the conventional art, clip applier for occlusion and ligation of vessels are well known.

Conventional clip appliers typically include an elongated body having a proximal end connected to an actuating mechanism, and a pair of jaws supported at the distal end.

In one exemplary embodiment of a conventional art clip applier, the jaws include a pair of opposing jaw members which are movable with respect to each other. In this regard, the jaws may be configured to grasp a target area (e.g., a section of body tissue) therebetween. Thus, the jaws are moved relative to each other when an operator operates an actuating handle coupled to an actuating mechanism. In some conventional art clip appliers, multiple surgical clips are supported in the elongated body and moved distally, one at a time, into the jaw members in preparation for being applied to a section of tissue.

There are several disadvantages associated with conventional clip appliers as described and as currently used. For example, conventional clip appliers have a rigid elongated body for receiving surgical clips therein. Therefore, these conventional clip appliers cannot extend through, e.g., an endoscope having an elongated channel that includes at least one curved portion.

Additionally, because of the rigid elongated body of the conventional clip applier, the distal end of the clip applier (e.g., proximate the jaws) may become damaged during assembly, transport, etc.

SUMMARY OF THE INVENTION

Accordingly, what is needed is an actuator of a clip applier which can be used in a clip applier having a flexible tool (e.g., so that the actuator can advance surgical clips provided within a clip applier having a flexible tool pass an elongated channel of, e.g., and endoscope that includes at least one curved portion. Further, what is also needed is a detachable connector which facilitates attachment of a distal end of a clip applier to a proximal end of a clip applier.

These and other features of the present disclosure will be apparent from review of the specification and accompanying drawings.

Accordingly, a non-limiting embodiment of the present invention provides a clip applier for deploying a surgical clip. In this regard, the clip applier includes an actuator having a flexible wire and a collet chuck coupled to a piston. Further, actuation of the piston in a forward direction towards a distal end of the clip applier advances the flexible wire in the forward direction. Additionally, a proximal end of the flexible wire may be positioned within the collet chuck.

Further, in accordance with another feature, the clip applier may also include a collet chuck ring at a circumference of a distal end of the collet chuck. In this regard, the collet chuck ring may be configured to apply a clamping force to the distal end of the collet chuck so as to clamp the proximal end of the flexible wire within the collet chuck.

Additionally, the clip applier may also include a tube push configured to operate a distal end of the clip applier. The collet chuck ring may be positioned within a slit of the tube push. Further, the slit may have a front end engagement surface. In this regard, when the collet chuck is advanced in the forward direction, the collet chuck ring may advance with the collect chuck until the collet chuck ring engages the front end engagement surface of the slit.

In yet still another feature, the clip applier may include a valve positioned intermediate the proximal end and a distal end of the flexible wire in an axial direction of the clip applier. Additionally, the valve may be positioned within the tube push and press-fitted within an opening of an inner coil pipe. Further, the inner coil pipe may be rotatably coupled (e.g., via a pin) to a rotator provided at a proximal end of the clip applier.

Further, in accordance with an additional feature, when the collet chuck returns in a rearward direction towards the proximal end of the clip applier, the collet chuck may release the flexible wire such that the flexible wire is generally stationarily supported within the valve relative to the valve.

Additionally, the clip applier may include a spacer positioned rearward of the collet chuck ring. In this regard, the collet chuck may be configured to clamp the proximal end of the flexible wire when the collet chuck ring engages the spacer.

In another feature of the present invention, the front end engagement surface of the slit includes an abutment face which extends generally perpendicular to a linear direction of movement of the collet chuck.

Additionally, actuation of the actuator may be configured to displace the collet chuck ring and the tube push in the forward direction. For example, an amount of the displacement of the collet chuck ring may be greater than an amount of the displacement of the tube push, i.e., such that the collet chuck ring engages the front end engagement surface of the slit. Additionally, the valve may be made of an elastomeric material.

Further, the actuator of the clip applier may include a handle and a trigger. In this regard, depression of the trigger may actuate the piston in the forward direction.

A non-limiting embodiment of the present invention also provides a clip applier for deploying a surgical clip. Further, the clip applier may include a shaft having a proximal end and a distal end. In this regard, the distal end of the shaft may include a flexible tool configured to receive the surgical clip. Additionally, a pair of jaws may be provided at a distal end of the flexible tool. Further, a tube push may be configured to open and close the pair of jaws. A rotator may be provided at a proximal end of the shaft. An actuator provided at the proximal end of the shaft and configured to advance the surgical clip within the flexible tool. Further, the clip applier may also include a detachable connector configured to detachably connect the flexible tool to the actuator.

For example, the detachable connector may include a screw cup, a sheath screw, and a keyed coil pipe. In this regard, a sheath screw projection of the sheath screw may be engageable with a coil pipe recess of the keyed coil pipe so as to rotatably couple the sheath screw to the keyed coil pipe. Additionally, a coil pipe projection may selectively engage a screw cup recess of the screw cup.

In yet another feature, the detachable connector may include a coil spring extending axially between the screw cup and keyed coil pipe. In this regard, a first end of the coil spring may engage an end-face of the screw cup and a second end of the coil spring may engage an end-face of the keyed coil pipe.

Furthermore, the screw may include a sheath connection end connectable to the inner coil pipe. In this regard, when the coil spring is in a first position, rotation of the screw cup rotates the keyed coil pipe and the sheath screw so that the connection end of the sheath screw is connected to the inner coil pipe. Additionally, the sheath screw may include a screw cup connection end connectable to a rotator connection end of the rotator. Further, when the coil spring is compressed to a second position, the screw cup recess may disengage the coil pipe projection such that rotation of the screw cup connects the screw cup connection end to the proximal end of the shaft without rotation of the keyed coil pipe and sheath screw. Additionally, the sheath connection end and the screw cup connection end may include threaded connectors.

According to another feature, an inner coil pipe of the clip applier may have an inner coil pipe connection end configured to receive the threaded sheath connection end. Additionally, an internal thread ring of the clip applier may be positioned at the rotator connection end of the rotator. In this regard, the threaded ring may be configured to receive the threaded screw cup connection end. Further, compression of the coil spring to the second position may be configured to axially offset the screw cup recess and the coil pipe projection.

BRIEF DESCRIPTION OF THE DRAWINGS

The present invention is further described in the detail description which follows, in reference to the noted plurality of drawings, by way of non-limiting examples of preferred embodiments of the present invention, in which like characters represent like elements throughout the several views of the drawings, and wherein:

FIG. 1B is an enlarged section view;

FIG. 4A is a top plan view of the flexible tool;

FIG. 4B is a cross-sectional view of the flexible tool of FIG. 4 taken along section A-A of FIG. 4A;

FIG. 5A is a detailed view of surgical clips positioned within the rails of the flexible tool;

FIG. 5B is an exploded view showing the surgical clip, connection point and rails in further detail;

FIGS. 7A-7E illustrate the flexible tool performing a surgical procedure for clamping a target area;

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1A:
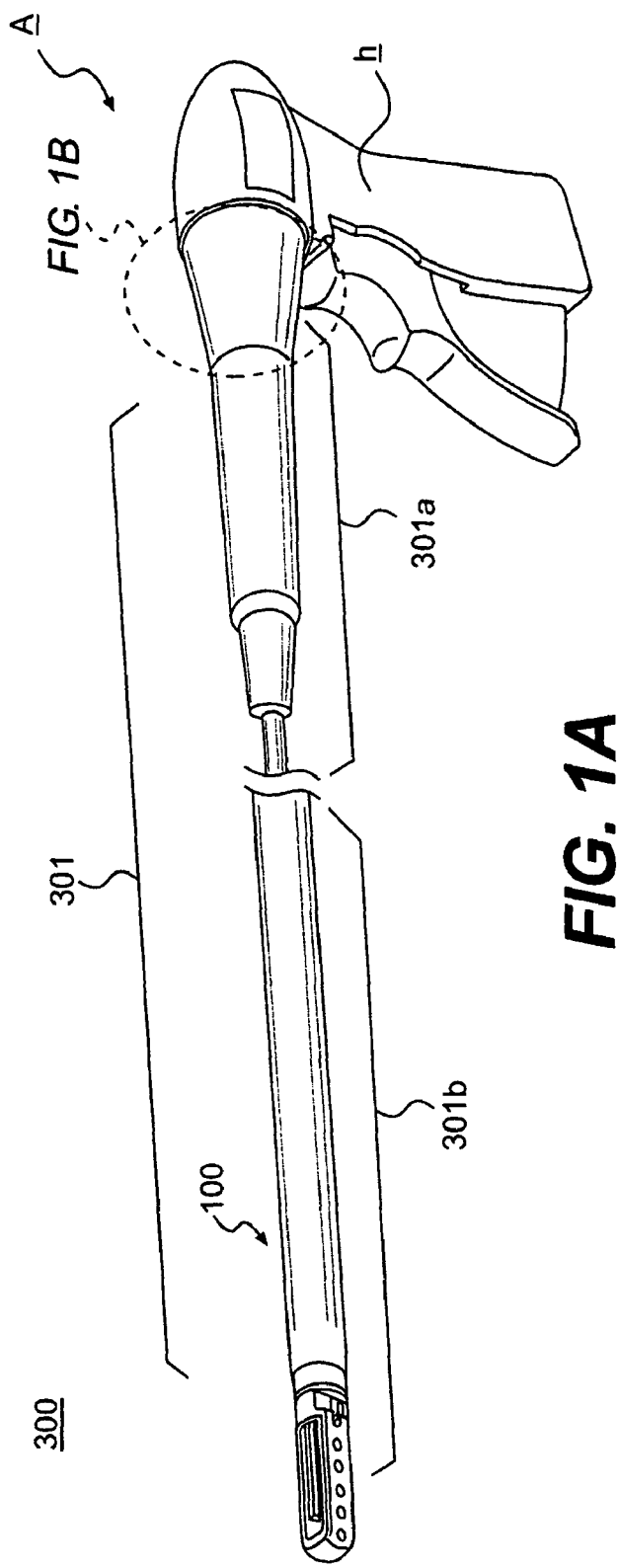
FIGS. 1A and 1B, FIG. 1A is a perspective view of a clip applier according to a non-limiting embodiment of the present invention.
Figure 1B:
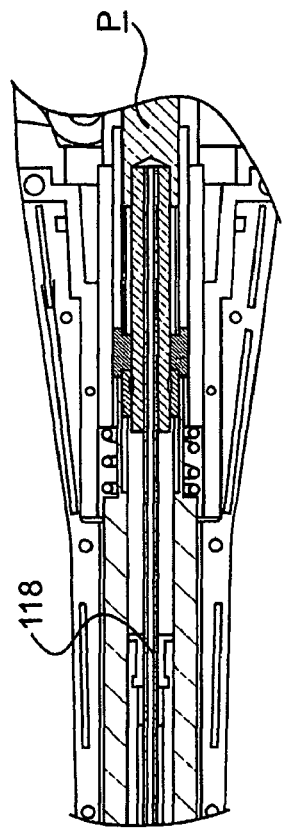
Figure 3:
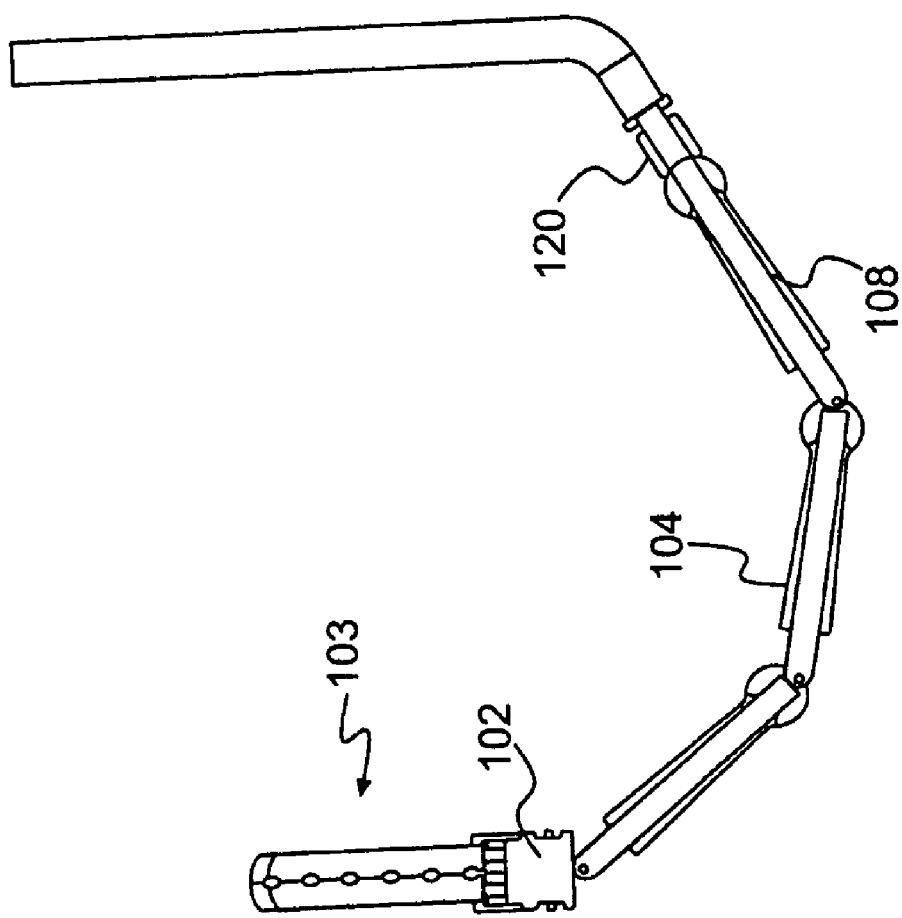
FIG. 3 is a side view of the flexible tool illustrating rails of the flexible tool articulated at connection points.

Referring to the drawings, FIG. 1 shows a flexible tool 100 of a clip applier 300 for applying a surgical clip (104, as shown in, e.g., FIG. 3) to a target area during a surgical procedure. In this regard, the clip applier 300 may include a shaft 301 having a proximal end 301a and a distal end 301b. Further, the distal end 301b of the shaft 301 may include the flexible tool 100. The flexible tool 100 may have at least two rails 108 connected to each other by at least one jointed connection 106 such that the rails 108 are configured to rotate about the jointed connection 106.

Additionally, as shown in FIGS. 2, 3, 4A and 4B, jaws 103 are provided at a distal end of the flexible tool 100. Further, as shown in FIG. 1, an actuator A may be provided at a proximal end 301a of the shaft 301. In this regard, the actuator A may be configured to open and close the jaws 103 (e.g., either directly or through a mechanism which couples an action of the actuator to movement of the jaws) and advance the surgical clip 104 within the flexible tool 100.

FIGS. 5A and 5B shows the flexible tool 100 having the plurality of rails 108 and the jointed connection 106 comprising a plurality of jointed connections (also 106). Therefore, it should be appreciated that the plurality of rails 108 may be provided in any number suitable for achieving a desired flexibility of the flexible tool 100. Additionally, the rails 108 (as well as surgical clips which are configured to be received therein) may also be of a length suitable to achieve the desired flexibility of the flexible tool 100.

In other words, the larger the number of rails 108, the more flexible the flexible tool 100 becomes. Similarly, the shorter the length of the rails 108, the more flexible the flexible tool 100 becomes. Referring again to FIGS. 5A and 5B, the jointed connection 106 may comprise any suitable connector which would allow the rails 108 to rotate about the connection 106; thereby further providing the flexible tool 100 with the desired flexibility. In other words, the plurality of rails 108 and jointed connections 106 are configured to allow the distal end 301b of the shaft to bend at various locations. In this regard, the jointed connection 106 may comprise a pin (also 106), a flexible material connecting adjacent rails, or a male/female connection.

However, one of ordinary skill in the art would recognize that other suitable connectors capable of providing flexibility to the tool may be employed without departing from the spirit and scope of the present invention.

Figure 8:
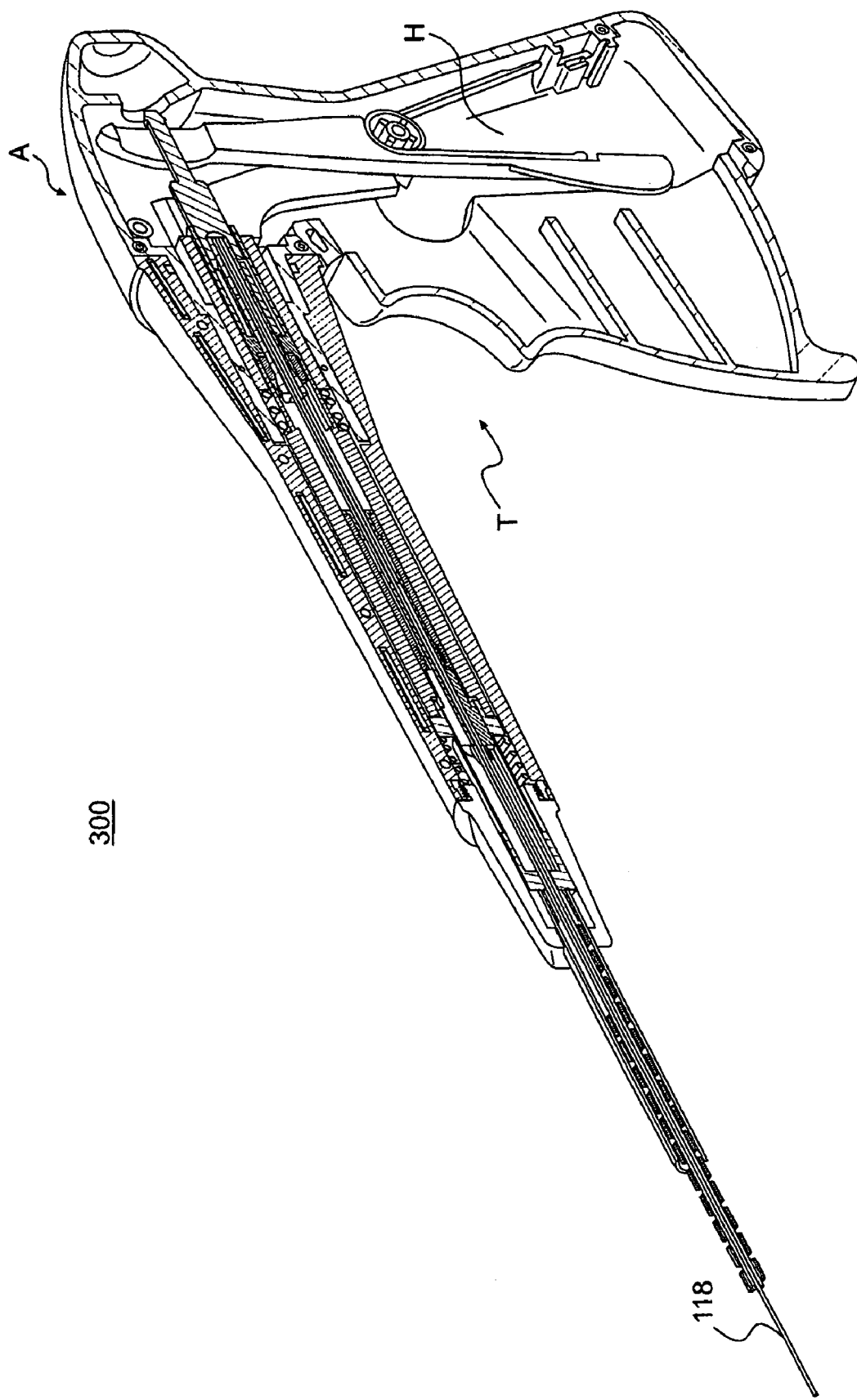
FIG. 8 is a cross-sectional view of a hand-piece of the clip applier.

Referring to FIG. 8, the flexible tool 100 (as shown in FIG. 1) may be coupled to an actuator A comprising a hand-piece H having a trigger T for actuating a flexible wire 118 in a forward direction (i.e., towards a distal end of the clip applier). In this regard, the actuator A may also include a flexible wire 118 connected to a pusher 120 and coupled to the hand-piece H. Therefore, both the flexible wire 118 and pusher 120 may be actuateable towards in a forward direction upon actuation of the handpiece H. Further, upon actuation, the pusher 120 may be configured to engage a rear surface of a proximal-most surgical clip 104 so as to advance the surgical clip(s) 104 within the flexible tool 100 and in the forward direction towards the jaws 103.

According to another feature, as shown in FIG. 8, the flexible wire may be connected to a suitable actuating mechanism, e.g. (a piston), which is configured to reciprocate linearly in a backwards and forward (i.e., proximal and distal) direction. In this regard, depression of a trigger T provided on the hand piece H may cause the piston P to be actuated linearly in a forward direction, thereby causing the flexible wire 118 and pusher 120 to be actuateable in the forward direction. More simply put, upon actuation of the piston P, the pusher 120 may be configured to engage a rear surface of a proximal-most surgical clip 104 so as to advance the surgical clip 104 within the flexible tool 100 and towards the jaw members 103a, 103b.

However, one of ordinary skill in the art would recognize that other suitable actuators capable of advancing the surgical clips with the flexible tool may be employed without departing from the spirit and scope of the present invention.

Additionally, as shown in FIGS. 4A and 4B, the flexible tool 100 may include an outer pipe 102 and an outer coil 101. In this regard, the outer pipe 102 may be configured to rotatably support the jaw members 103a, 103b and the outer coil 101 may provide an outer resilient covering of the flexible tool 100. In this regard, a proximal end of the outer pipe 102 may be connected to a distal end of the outer coil 101 by any suitable connection (e.g., by welding or adhesive). As illustrated in FIGS. 6A-6F, the outer pipe 102 may move in the forward direction so that the jaw members 103a, 103b rotate to a closed position (see FIGS. 6A and 6B), and the outer pipe 102 may move in the rearward direction so that the jaw members 103a, 103b rotate towards an opened position (see FIGS. 6C and 6D).

Additionally, as shown in FIGS. 6A-6D, the outer pipe 102 may be configured to rotatably support the jaw members 103a, 103b and the outer coil 101 may comprise the outer covering of the flexible tool 100.

Figure 6A:
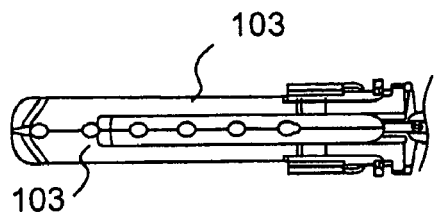
FIGS. 6A-6F are perspective views of various opened and closed positions of jaws of the flexible tool of the present invention.
Figure 6B:
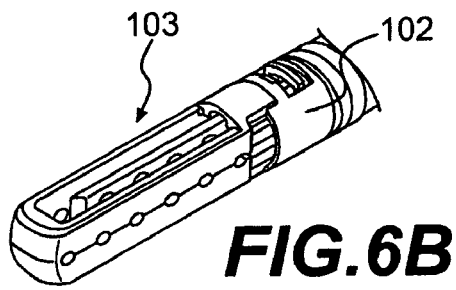
Figure 6C:
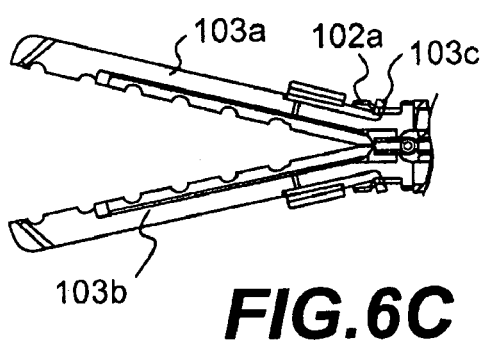
Figure 6D:
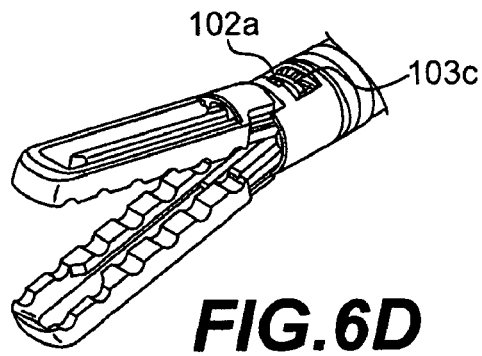
Figure 6E:
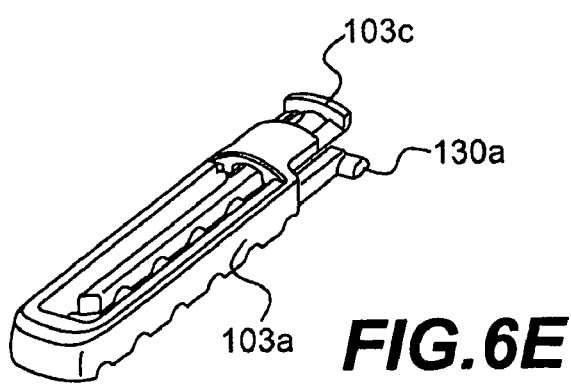

Additionally, as shown in FIG. 6E, a projection 130a may be provided at a proximal end of the jaws 103 and a receiving aperture provided at a distal end of a distal-most rail 108. In this regard, the projection 130a may be received within the receiving aperture 130b (as shown in FIG. 5A) thereby rotatably coupling the jaw members 103a to the distal-most rail 108.

Figure 6F:
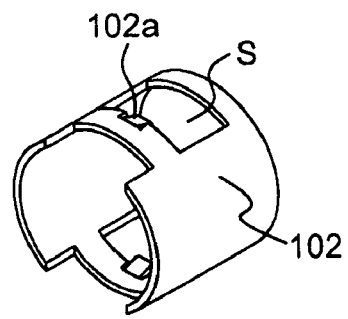

According to another feature of the present invention, as shown in FIG. 6F, since a rear end 103c of the jaws 103 (e.g., comprising a protrusion) may be inserted into a receiving aperture S (or slit) of the outer pipe, the jaws 103 may be configured to rotate as the outer pipe 102 reciprocates. In this regard, the outer pipe protrusion 102a proximate the rear ends of the jaws 103 may engage the rear end of jaws 103; thereby, causing the jaw members 103a, 103b to rotate.

Figure 2:
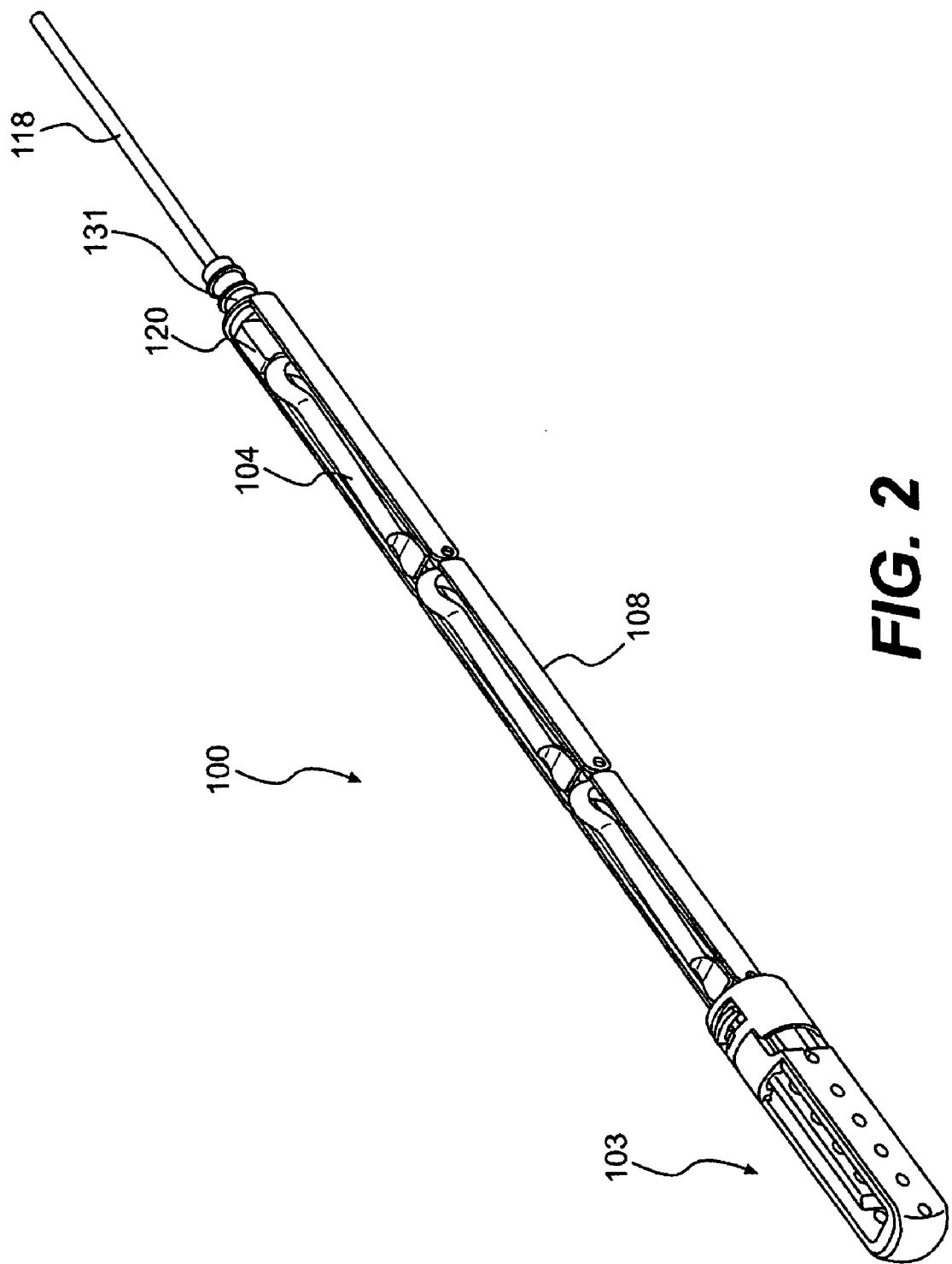
FIG. 2 is a perspective view of a flexible tool of the clip applier according to a non-limiting embodiment of the present invention.

Additionally, as illustrated in FIG. 2, the pusher 120 may be positioned between the rails 108. In this regard, the pusher 120 may be rotated about a longitudinal axis of the shaft 301 by rotating the flexible wire 118 connected to the pusher 120. Further, since a sheath 131 may be press-fitted (or otherwise fitted) to the rear end of the proximal-most rail 108, the sheath 131 may rotate concurrently with the rails 108. Further, since the pusher 120, the flexible wire 118, and the rails 108 are all coupled to each other, the flexible tool 100 may be rotated by rotating the outer coil 100, the flexible wire 118 and/or the sheath 131.

Further, as illustrated in FIGS. 2 and 5B, a length of the surgical clip 104 may be approximately the same as a length of the rails 108. According to another feature, and as shown in FIG. 7D each jaw may comprise an inwardly projecting ledge 109. In this regard, the ledge 109 may be configured to project inwardly from an inner surface of a corresponding jaw member 103a, 103b so as to engage the surgical clip 104 and temporarily expand the surgical clip 104 from a pre-biased closed position to an open position in order to clamp the target area (see, FIGS. 7A-7E).

In more exemplary detail, the jaws 103 may be actuated so as to clamp a target area TA therebetween. Subsequent to clamping the target area TA, the distal-most surgical clip 104 may be advanced such that a front end thereof engages the projecting ledge 109 (e.g., as the front end of the surgical clip 104 is advanced along the projecting ledges), thereby expanding the surgical clip 104 to an opened position from the pre-biased closed position. Further, the surgical clip 104 may return to the pre-biased closed position after the surgical clip 104 advances pass a point where the projecting ledge 109 terminates; whereupon the surgical clip 104 is allowed to return to a pre-biased closed position and clamp the target area TA therebetween. Further, the jaws 103 may be actuated to an opened position so as to release the target area TA, while the surgical clip 104 continues to clamp target area TA.

Now referring to FIGS. 1 and 2, the flexible tool 100 may be detachably coupled to the proximal end of the shaft 301a.

Referring to FIGS. 2 and 4a, at least one of the outer coil 101, flexible wire 118 and a sheath 131, press-fitted to a rear end of the flexible tool 100, may be configured to rotate the flexible tool 100.

With reference to FIGS. 7A-7E, operation of the clip applier is explained in further detail. Referring now to FIG. 7A, when no force is exerted on the clip 104, the clip is in a closed position because the clip 104 is pre-biased towards a closed position, much like a bobby pin. Therefore, when the clip 104 engages the rails 109 of the jaws 103 the clip 104 is urged to open so as to prepare to, e.g., engage, receive or clamp tissue positioned between the jaws (see FIG. 7C).

In this regard, as discussed supra, when the clip 104 is advanced forward to a portion of the jaws 103 which does not include the inwardly projecting ledge 109 (e.g., a position where the inwardly projecting ledge 109 terminates), the surgical clip 104 disengages the ledge 109, and, as a result, the surgical clip 104 is allowed to return to its pre-biased closed position; thereby clamping the tissue held between the jaws (see FIG. 7E).

In this regard, the jaws 103 may be configured to pivot about a support to opened and closed positions. For example, as shown in FIG. 7B the jaws 103 may pivot in the closing direction when the outer pipe 102 moves forward and comes in contact with the jaws 103. Further, when the outer pipe 102 moves in the rearward (or proximal) direction (i.e., opposing the forward, or distal, direction) the jaws may be opened (see FIG. 7E). In this regard, the outer pipe 102 may be provided with the outer pipe protrusion 102a which is configured to engage at least one of the jaw members 103a or 103b. For example, the outer pipe protrusion 102a may come into contact with a proximal end portion of at least one of the jaws 103 (see FIG. 6D), thereby pivoting the jaw members 103a, 103b to an open position. Additionally, a front end of the outer pipe 102, when actuated in a forward direction, may engage surfaces of the jaws 103 in order to rotate the jaws to a closed position (see FIG. 6A).

More simply put, the outer pipe 102 may be provided with cam surfaces which engage the jaw members 103a, 103b in order to open and close the jaws 103.

However, one of ordinary skill in the art would recognize that other suitable mechanisms for opening and closing the jaws may be employed without departing from the spirit and scope of the present invention.

FIGS. 7A-7E show a procedure for clamping a target area TA. For example, the surgical clip applier 300 may approach a target area TA and clamp the target area TA by moving the outer coil 101 and outer pipe 102 forward, thereby closing the jaw members 103a, 103b. Subsequently, the pusher 120 may be actuated in the forward direction in order to advance the surgical clip 104 within the flexible tool 100. For example, at this point, the surgical clip 104 may be advanced forward to a portion of the jaws 103 which does not include the jaw rails (see FIG. 7D). In this regard, the surgical clip 104 may then disengage the jaw rail 109, and clamp the target area TA held by the jaw members 103a, 103b, since the surgical clip 104 is pre-biased towards its closed position.

Further, when the jaw members 103a, 103b are opened after deployment of the surgical clip 104, the clip applier 103 can be removed from the target area TA, leaving the surgical clip 104 in place (FIG. 7E).

Additionally, the present invention allows for the clip applier 300 to have a diameter of about 3 mm to 5 mm and a length of about 1 to 2 meters, i.e., in order to provide a flexible minimally-invasive clip applier, although those of skill in the art would appreciate that the clip applier would have other suitable diameters and lengths. As discussed in further detail below, the flexible clip applier 300 can be inserted into the channel 400a of an endoscope 400 (see FIG. 9) and the flexible tool 100 may include a small cartridge, for example, having three surgical clips (see FIG. 10); although any suitable desirable number of surgical clips may be provided within the cartridge. In this regard, due to the size and dimension of the flexible tool 100, the flexible tool (as well as the surgical clip cartridge) may be provided to be detachable and disposable (e.g., as shown in FIG. 2).

Figure 9:
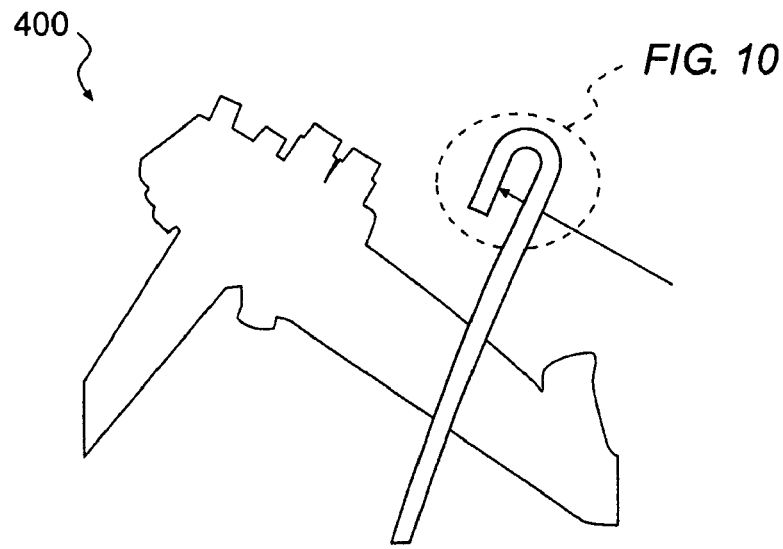
FIG. 9 is a perspective view of an endoscope for performing a minimally invasive surgical procedure.
Figure 10:
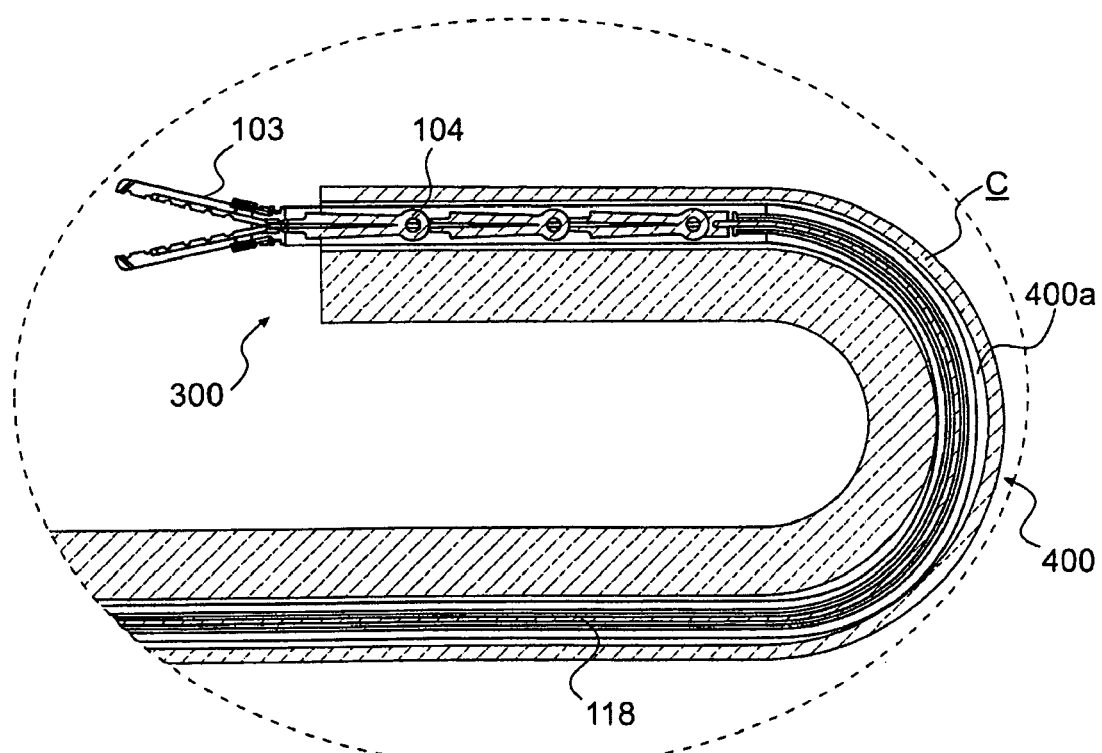
FIG. 10 is a cross-sectional view of the clip applier of the present invention inserted within an elongated channel of the endoscope.

Further, it should also be appreciated that the clip applier 300 of the present invention can be used as part of a surgical assembly (see FIGS. 9 and 10). For example, FIG. 10 illustrates a surgical assembly including an endoscope 400 having an elongated channel 400a, at least one surgical clip 104, and a clip applier 300. In this regard, as discussed above, the clip applier 300 may include a shaft 301 having a proximal end 301a and a distal end 301b. The distal end 301b of the shaft 301 may include a flexible tool 100 having at least two rails 108 which are connected to each other by at least one jointed connection 106. Similar to the description above, the rails 108 may be configured to rotate about the jointed connection 106 and the flexible tool 100 may be configured to be inserted within the channel 400a of the endoscope 400. Additionally, the jaws 103 may be provided at a distal end of the flexible tool 100, and an actuator A (e.g., a hand piece or any other suitable actuating mechanism) provided at the proximal end of the shaft 301a, the actuator A configured to advance the surgical clip 104 within the flexible tool 100. Additionally, the flexible tool 100 may be configured to extend past a longitudinally curved region C of the channel 400a of the endoscope 400, e.g., as illustrated in FIG. 10.

Figure 11A:
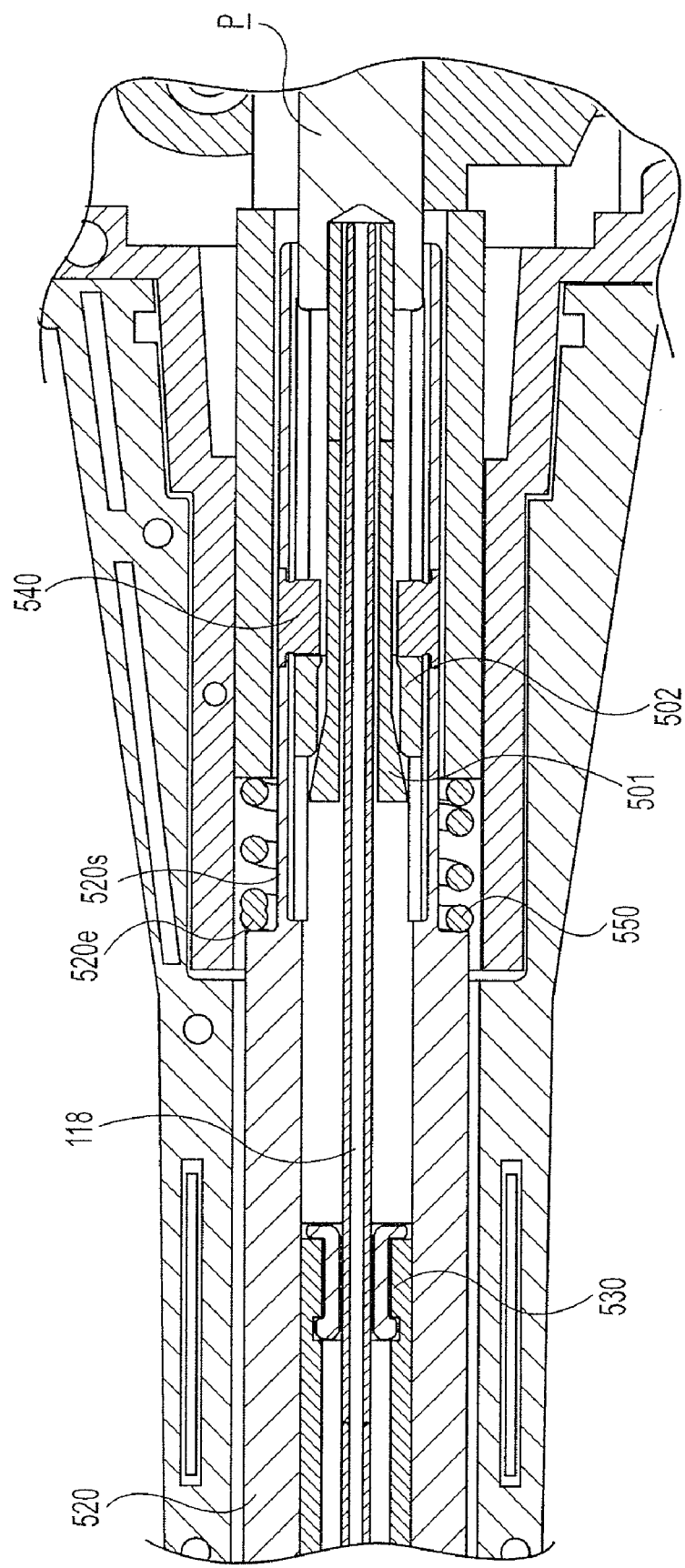
FIG. 11A is a cross-sectional view of the actuator of the clip applier of the present invention.

Discussing the actuator A in further detail, as shown in FIG. 11A, the clip applier may comprise an actuator having a flexible wire 118, as discussed supra, and a collet chuck 501 coupled to a piston P. In this regard, actuation of the piston P in a forward direction, towards a distal end of the clip applier, advances the flexible wire 118 in the forward direction.

A proximal end of the flexible wire 118 may be positioned within the collet chuck 501. However, it should be appreciated, by one of ordinary skill in the art, that the flexible wire 118 may be coupled to the collet chuck 501 in any suitable manner; i.e., which would allow actuation of the collet chuck 501 in the forward direction to advance the flexible wire 118 forward.

Additionally, as shown in FIG. 11A, a collet chuck ring 502 may be provided at a circumference of a distal end of the collet chuck 501. In this regard, the collet chuck ring 502 may be configured to apply a clamping force to the distal end of the collet chuck 501 so as to clamp the proximal end of the flexible wire 118 within the collet chuck 501.

Figure 11B:
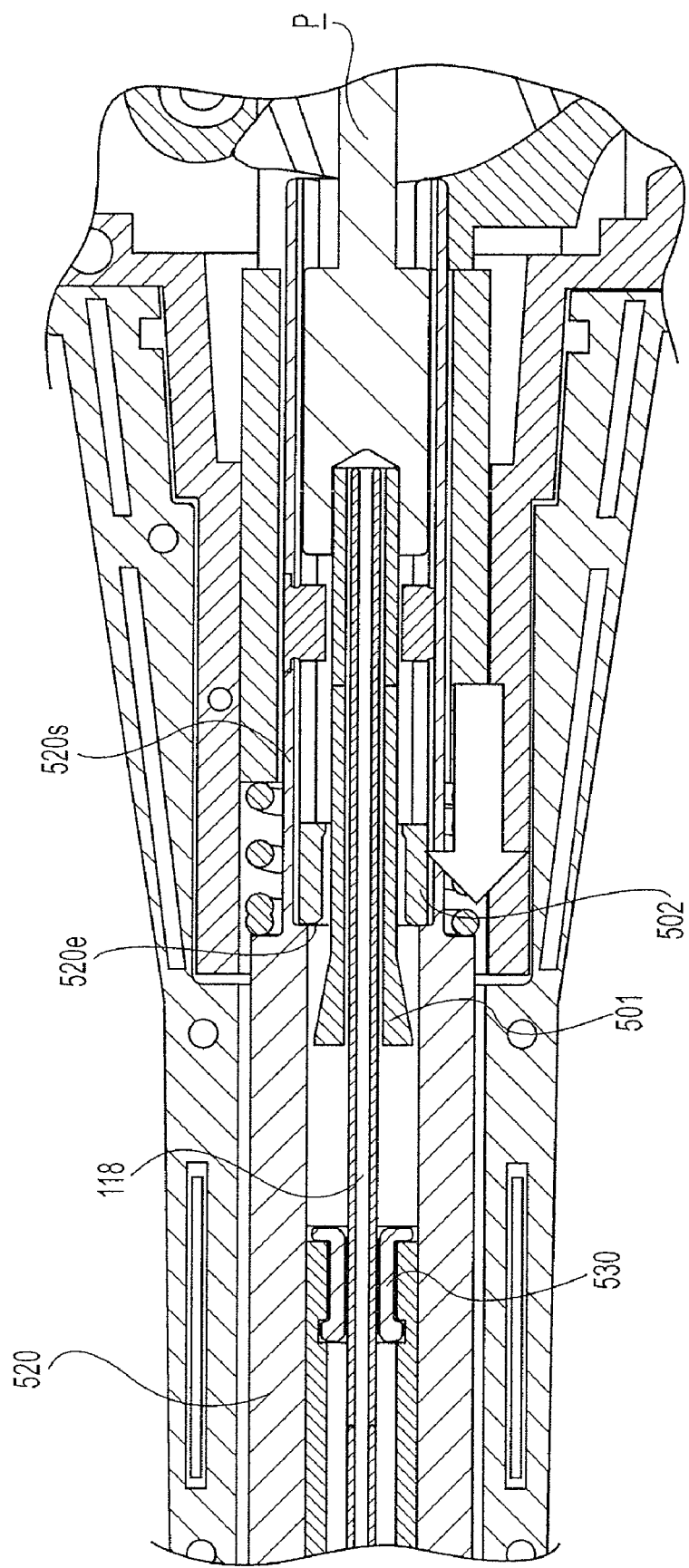
FIG. 11B is a cross-sectional view of the actuator of the clip applier of the present invention which shows the collect chuck being actuated in a forward direction of the clip applier.

Referring to FIG. 11B, a tube push 520 may be configured to operate a distal end of the clip applier. Further, the collet chuck ring 502 may be positioned within a slit 520s of the tube push 520.

Therefore, when the actuator A is actuated to advance the collet chuck 501 in the forward direction, the collet chuck ring 502 may advance with the collet chuck 501 until the collet chuck ring 502 engages the front end engagement surface 520e of the slit 520s, as shown in FIG. 11B. After the collet chuck ring 502 engages the front end engagement surface 520e of the slit 520s, the collet chuck 501 may advance, without the collet chuck ring 502, pass the front end engagement surface 520e of the slit 520s.

Additionally, referring to FIG. 11B, a valve 530 may be positioned intermediate the proximal end and a distal end of the flexible wire 118 in an axial direction of the clip applier. Therefore, after collet chuck ring 501 engages the front end engagement surface 520e of the slit 520s, and the collet chuck 501 continues to advance, the flexible wire 118 is advanced a corresponding amount within the valve 530.

In this regard, the valve 530 may utilize friction to support and retain the flexible wire 118 therein at the position to which the flexible wire 118 is advanced by the collet chuck 501. Further, because the collet chuck 501 is no longer clamped by the collet chuck ring 502 when the collet chuck 501 is advanced to its forwardmost point (i.e., to a point forward of the front end engagement surface 520e of the slit 520s), the clamping force on the collet chuck 502 is released. Therefore, when the collet chuck 502 returns toward the proximal end of the clip applier, as shown in FIG. 11C, the flexible wire 118 remains stationary supported within the valve 530 at the position to which the flexible wire 118 was advanced by the collect chuck 502.

Further, the valve 502 may include an elastomeric material such as silicon rubber, or any other suitable-material. Additionally, the valve 502 may be positioned within the tube push 520 and press-fitted within an opening of an inner coil pipe 605. Further, the inner coil pipe 605 may be rotatably coupled (e.g., via a pin 802) to a rotator 800 provided at a proximal end of the clip applier.

Figure 11C:
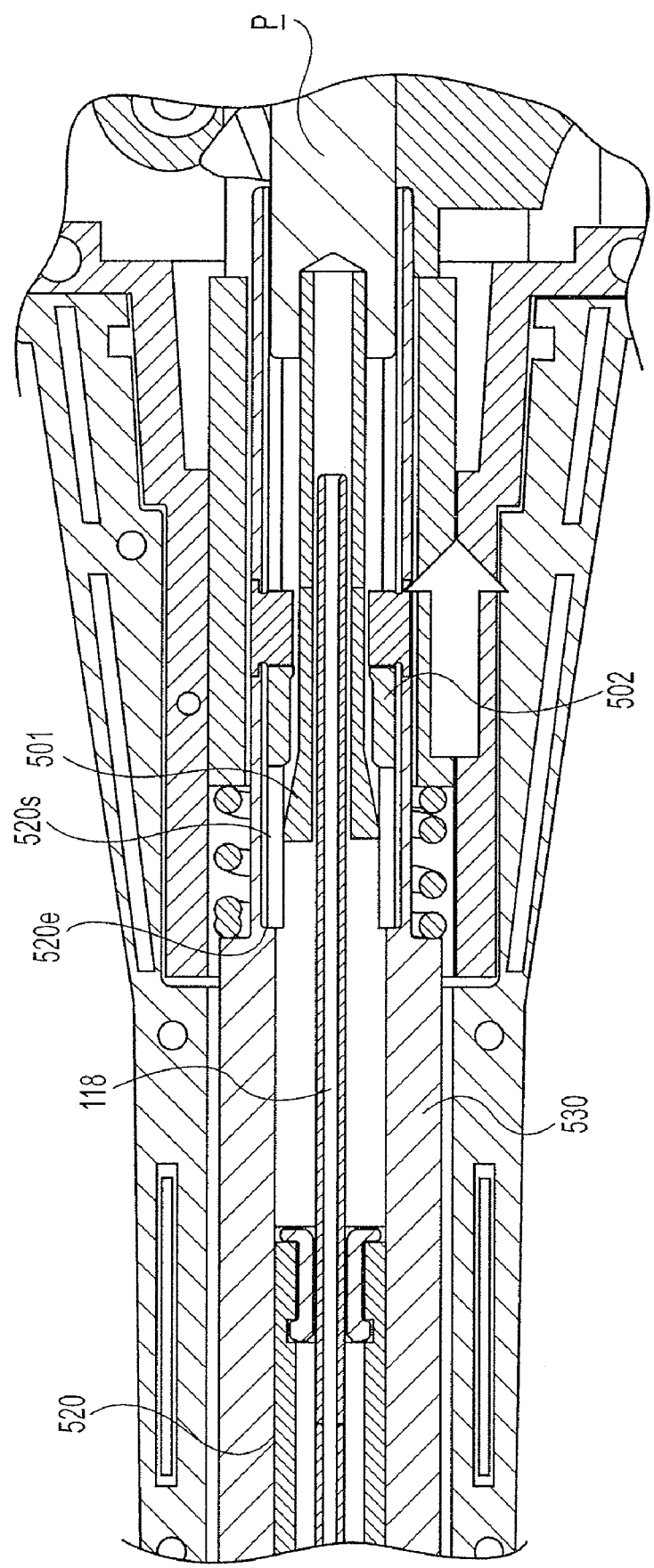
FIG. 11C is a cross-sectional view of the actuator of the clip applier of the present invention which shows the collect chuck returning towards a proximal end of the clip applier.

Referring to FIGS. 11A-11C, a spacer 540 may be positioned rearward of the collect chuck ring 502. In this regard, when the collet chuck ring 502 returns toward a rearward most position of the clip applier, the collet chuck 501 may be configured to again clamp the proximal end of the flexible wire 118 when the collet chuck ring 502 engages the spacer 540.

Accordingly, the sequence for advancing the flexible wire 118 can be carried out repeatedly in order to advance the surgical clips within the clip applier.

Further, actuation of the actuator A may be configured to displace the collet chuck ring 502 a greater amount in the forward direction than an amount of displacement of the tube push 520 in the forward direction.

As shown in FIGS. 11A-11C, an end of the tube push may receive an urging force from a tube push coil ring 550. In this regard, tube push coil ring 550 may be configured to displace the tube push 520, as well as the slit 520s, in the forward direction when the A is actuated. Further, the piston P may be configured to displace the collet chuck 501, as well as the collet chuck ring 502, in the forward direction when the piston P is actuated by the actuator. Therefore, it should be appreciated that the tube push 520 and the collet chuck ring 502 can be displaced by differing amounts. Thus, the actuator A may be configured to displace the collet chuck ring 502 a greater amount in the forward direction than an amount of displacement of the tube push 520 in the forward direction.

Further, it should be noted that the particulars of actuating the tube push in a forward direction, e.g., by using a paddle, are described in U.S. patent application Ser. No. 11/210,837 which has published as U.S. Patent Application No. 2007/0049950 and shares a common assignee with the present Application, the disclosure of which is expressly incorporated herein by reference thereto.

Referring to FIGS. 12A-12D, a detachable connector 600 may be provided to detachably connect the flexible tool to the actuator A. In this regard, the detachable connector 600 may include a screw cup 601, a sheath screw 603, a rotator 800 provided at a proximal end of the shaft, and a keyed coil pipe 602. Further, the sheath screw 603 may be provided with a sheath screw projection 603a which engages a coil pipe recess 602a of the keyed coil pipe 602 so as to rotatably couple the sheath screw 603 to the keyed coil pipe 602. Additionally, a coil pipe projection 602b of the coil pipe 602 may selectively engage a screw cup recess 601a of the screw cup 601.

Figure 12A:
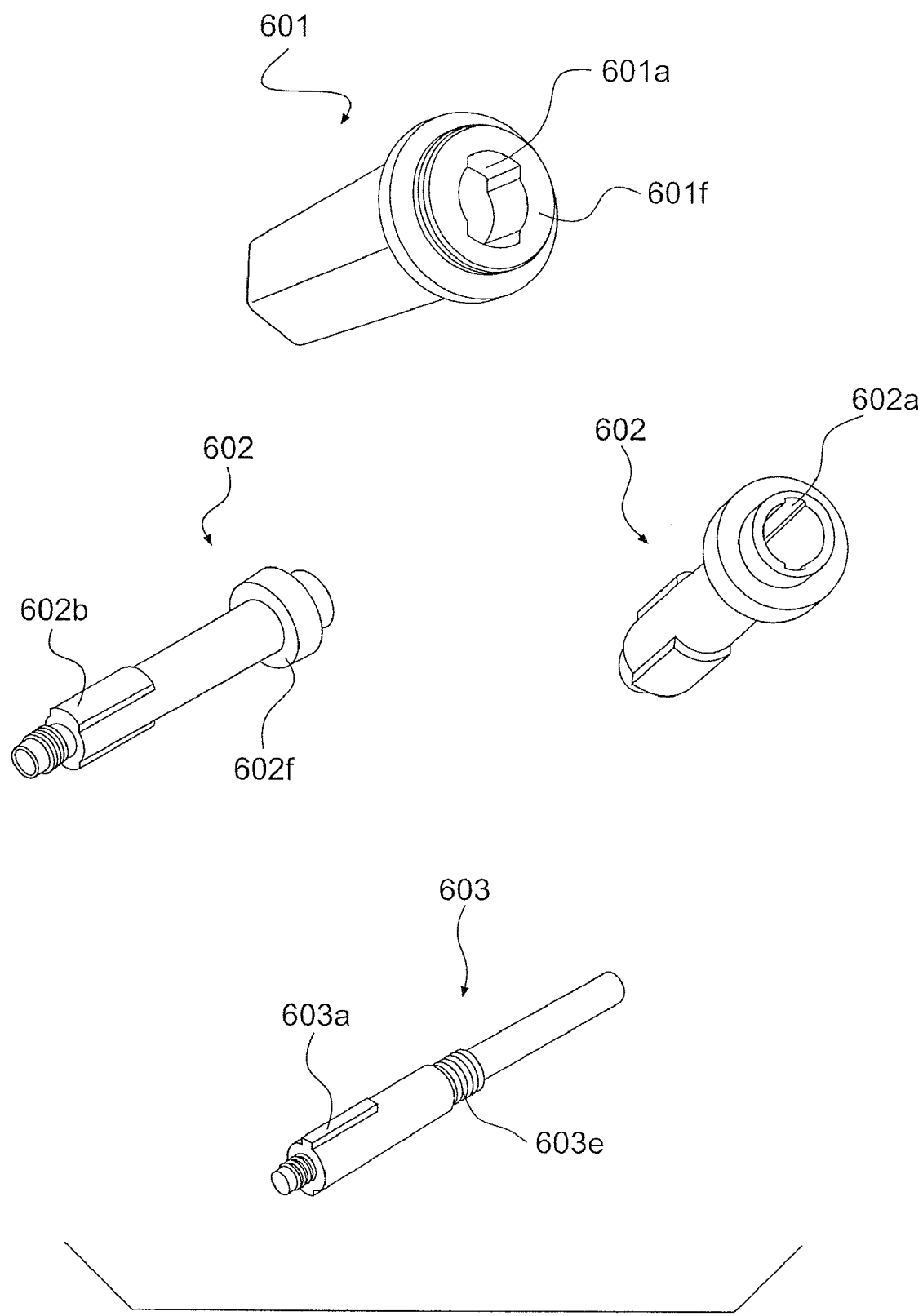
FIG. 12A is an exploded view of the components of the detachable connector of the clip applier of the present invention.
Figure 12B:
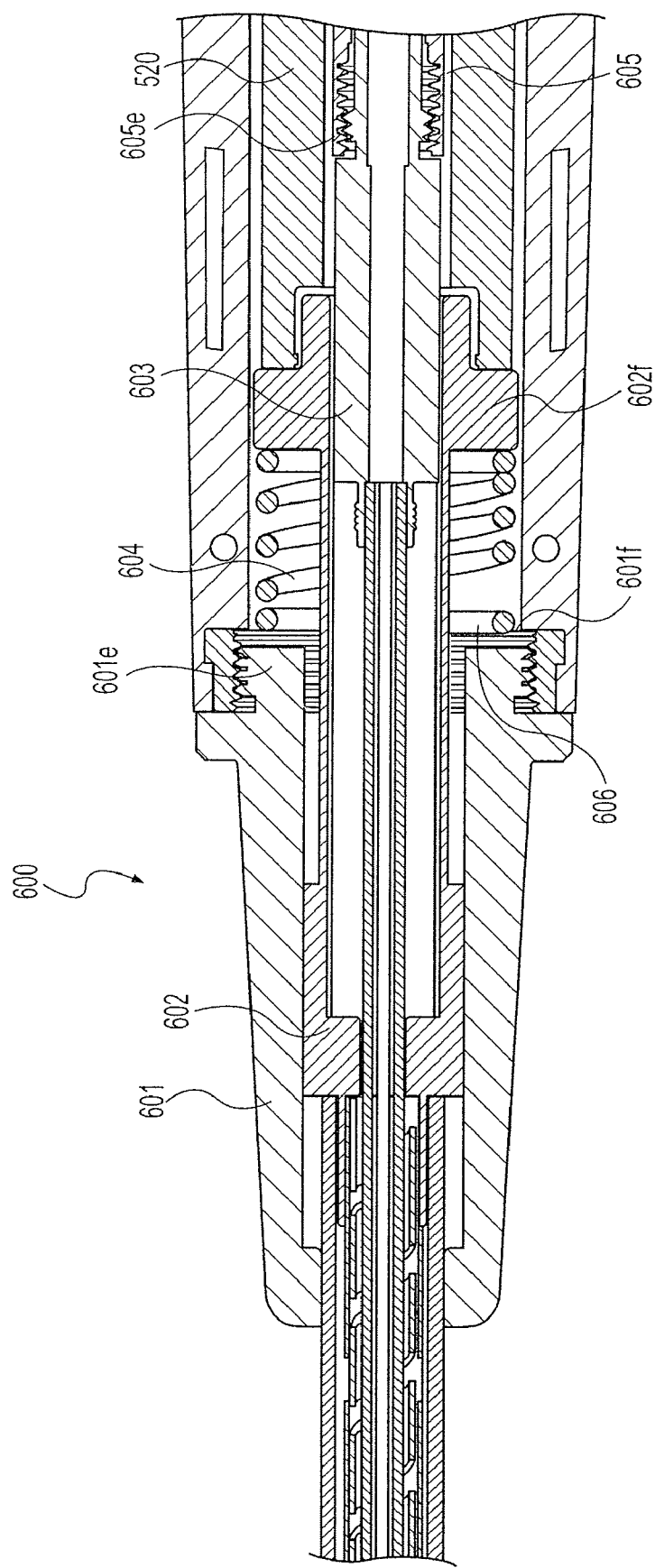
FIG. 12B is a cross-sectional view of the detachable connector of the clip applier of the present invention.
Figure 12C:
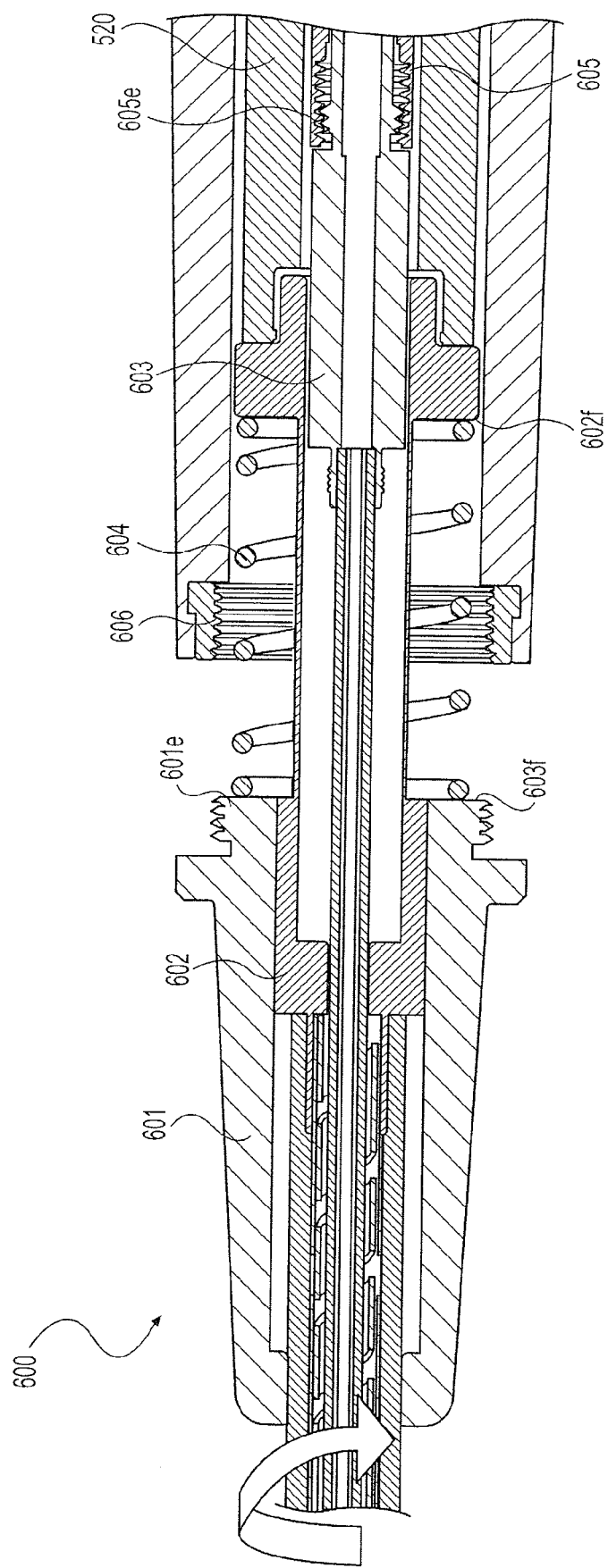
FIG. 12C is a cross-sectional view of the detachable connector of the clip applier of the present invention showing the screw cup in a first position and rotatably coupled to the sheath screw and keyed coil pipe.
Figure 12D:
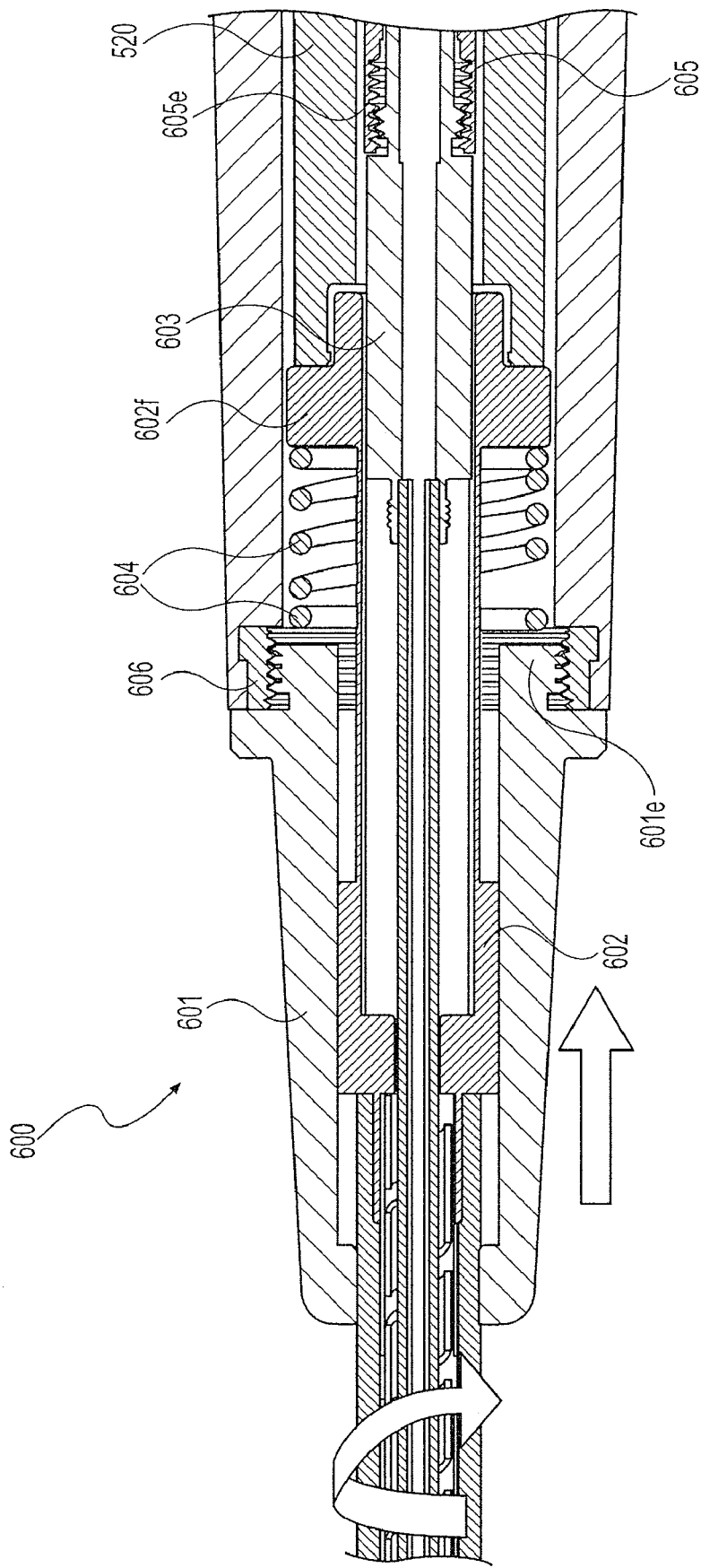
FIG. 12D is a cross-sectional view of the detachable connector of the clip applier of the present invention showing the screw cup in a second position and rotating independently of the sheath screw and keyed coil pipe.

Further, as shown in FIGS. 12B-12D, the detachable connector 600 may include a coil spring 604 extending axially between the screw cup 601 and keyed coil pipe 602. For example, a first end of the coil spring 604 may engage an end-face 601f of the screw cup 601 and a second end of the coil spring 604 may engage an end-face 602f of the keyed coil pipe 602.

Figure 13A:
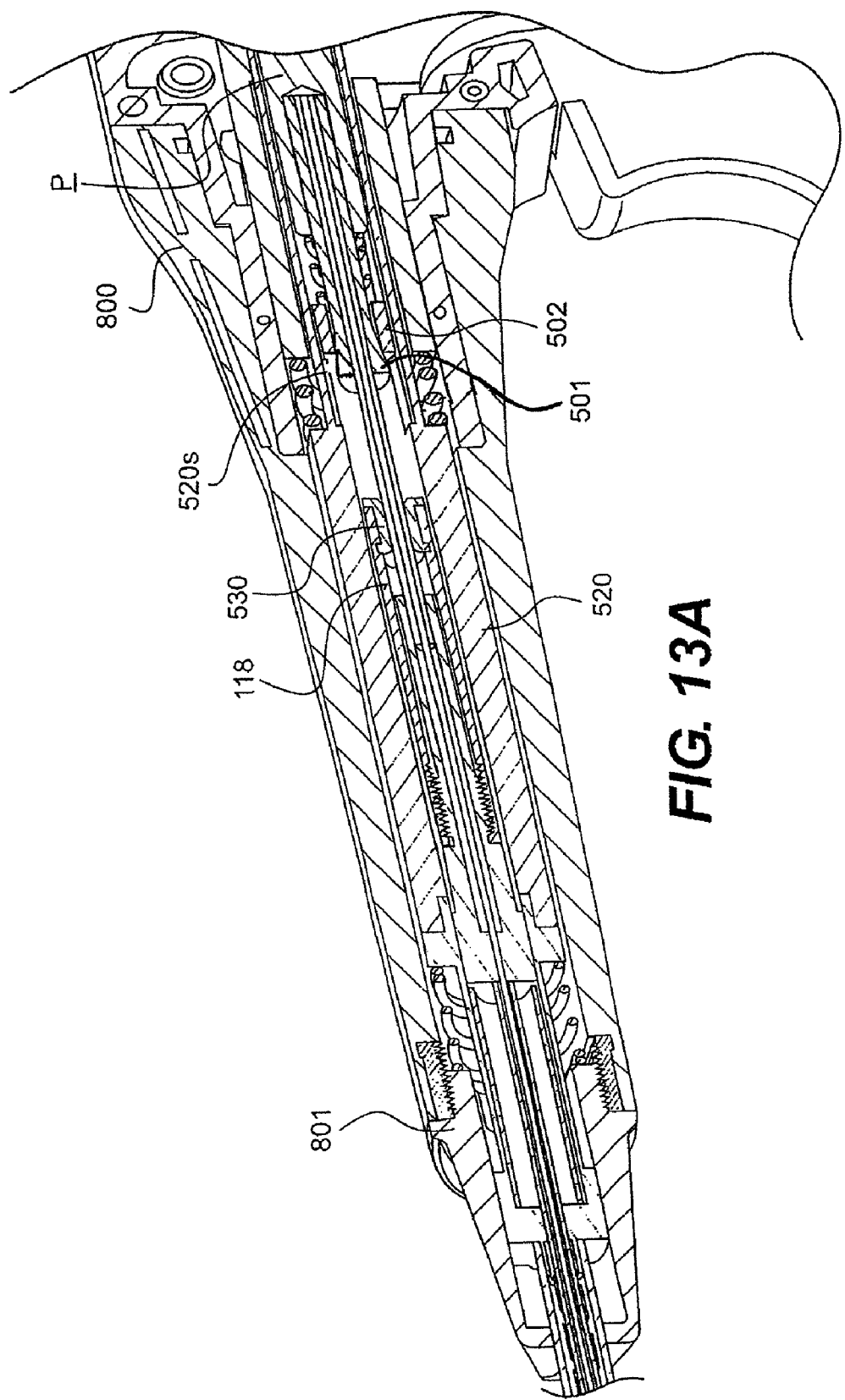
FIG. 13A is a cross-sectional view of the actuator and detachable connector of the present invention.
Figure 13B:
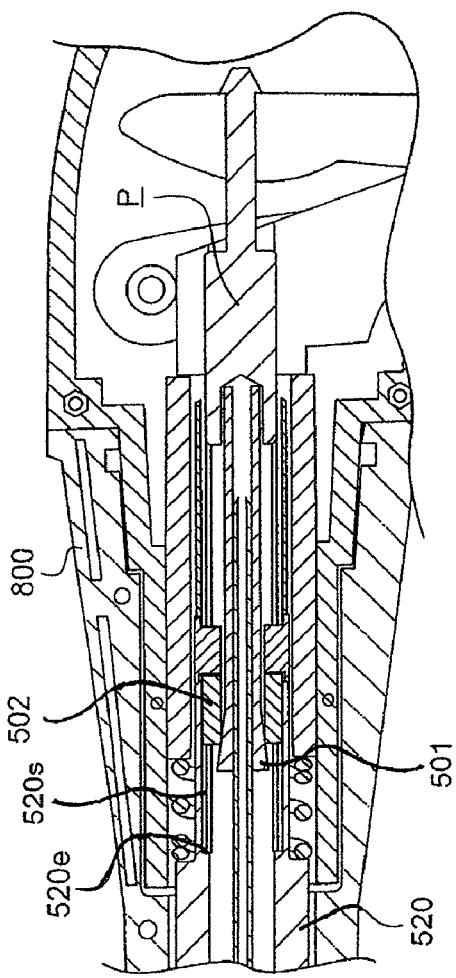
FIG. 13B is a cross-sectional view of the actuator and rotator of the present invention.
Figure 13C:
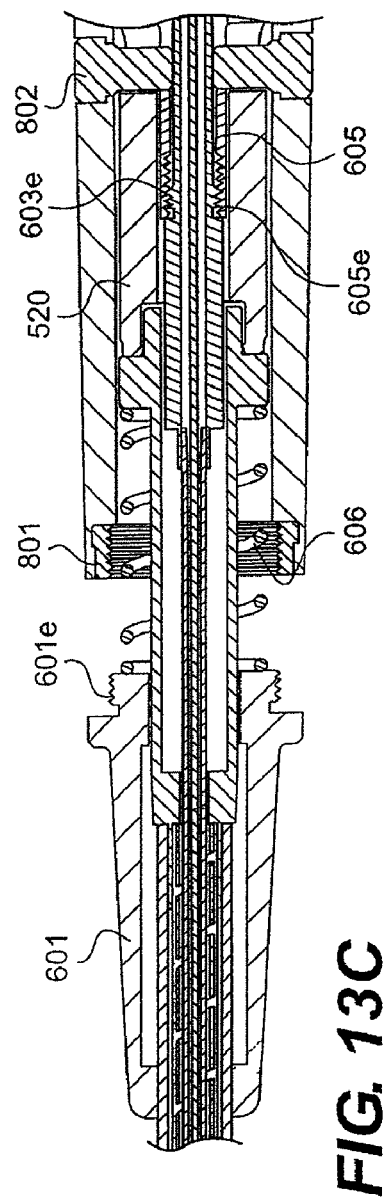
FIG. 13C is a cross-sectional view of the connection end of the rotator and screw cup of the present invention.

Referring to FIG. 12C, a sheath connection end 603e of the sheath screw 603 may be connected to the inner coil pipe 605 such that when the coil spring 604 is in a first position, rotation of the screw cup 601 rotates the keyed coil pipe 602 and the sheath screw 603, the connection end of the sheath screw 603e is connected to the inner coil pipe 605. Further, the screw cup 601 may include a screw cup connection end 601e connected to a rotator connection end 801 of the rotator 800 (e.g., as shown in FIGS. 13A-13C). In this regard, when the coil spring 604 is compressed to a second position (see FIG. 12D) the screw cup recess 601a may disengage the coil pipe projection such that rotation of the screw cup 601 connects the screw cup connection end 601e to the rotator connection end (see FIG. 13C), i.e., without rotation of the keyed coil pipe 602 and sheath screw 603.

Additionally, the sheath connection end 603e and the screw cup connection end 601e may include threaded connectors (see FIGS. 12A-12D). Further, the inner coil pipe 605 may have an inner coil pipe connection end 605e configured to receive the threaded sheath connection end 603e. Further, an internal thread ring 606 may be positioned at the rotator connection end and configured to receive the threaded screw cup connection end 601e.

Additionally, compression of the coil spring 604 to the second position may configured to axially offset the screw cup recess 601a and the coil pipe projection 602b, thereby allowing the screw cup 601 to be rotated independently of the sheath screw 603 and keyed coil pipe 602.

It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A clip applier for deploying a surgical clip, the clip applier comprising:
    an actuator configured to advance the surgical clip within the clip applier, the actuator comprising:
        a flexible wire;
        a collet chuck; and
        a piston coupled to the collet chuck, the collet chuck receiving and clamping a proximal end of the flexible wire at an initial position, wherein actuation of the piston in a forward direction towards a distal end of the clip applier advances both the collet chuck and flexible wire in the forward direction, and
        the collet chuck configured to release a clamping force applied to the end of the flexible wire so that the flexible wire remains positioned at an advanced position when the collet chuck returns in a rearward direction toward the initial position; and
    a valve positioned intermediate a distal end of the flexible wire and the proximal end of the flexible wire, wherein the valve generally stationarily supports the flexible wire at the advanced position when the collet chuck releases the clamping force.

2. The clip applier according to claim 1, further comprising a collet chuck ring at a circumference of a distal end of the collet chuck, the collet chuck ring configured to apply a clamping force to the distal end of the collet chuck so as to clamp the proximal end of the flexible wire within the collet chuck.

3. The clip applier according to claim 2, further comprising a tube push configured to operate a distal end of the clip applier, wherein:
- the collet chuck ring is positioned within a slit of the tube push;
- the slit having a front end engagement surface; and
- when the collet chuck is advanced in the forward direction, the collect chuck ring advances with the collect chuck until the collet chuck ring engages the front end engagement surface of the slit.

4. The clip applier according to claim 3, wherein the valve is positioned within the tube push and press-fitted within an opening of an inner coil pipe, and the inner coil pipe being rotatably coupled to a rotator provided at a proximal end of the clip applier.

5. The clip applier according to claim 4, wherein the valve is elastomeric.

6. The clip applier according to claim 3, the front end engagement surface of the slit comprising a abutment face which extends generally perpendicular to a linear direction of movement of the collet chuck.

7. The clip applier according to claim 3, wherein actuation of the actuator is configured to displace the collet chuck ring and the tube push in the forward direction, wherein an amount of the displacement of the collet chuck ring is greater than an amount of the displacement of the tube push such that the collet chuck ring engages the front end engagement surface of the slit.

8. The clip applier according to claim 3, further comprising a spacer positioned rearward of the collect chuck ring, wherein the collet chuck is configured to clamp the proximal end of the flexible wire when the collet chuck ring engages the spacer.

9. The clip applier according to claim 1, wherein the actuator further comprises a handle and a trigger.

10. The clip applier according to claim 9, wherein depression of the trigger actuates the piston in the forward direction.

* * * * *